United States Patent [19]
Atamian et al.

[11] Patent Number: 6,105,535
[45] Date of Patent: Aug. 22, 2000

[54] ANT HABITAT WITH RETAINER LIP

[75] Inventors: George C. Atamian, Upland; Brian A. Mehler, Long Beach, both of Calif.

[73] Assignee: Educational Insights, Inc., Carson, Calif.

[21] Appl. No.: 09/012,253

[22] Filed: Jan. 23, 1998

[51] Int. Cl.[7] .................................................. A01K 29/00
[52] U.S. Cl. .......................................... 119/6.5; 119/246
[58] Field of Search ............................ 119/6.5, 246, 247, 119/248, 61, 421; 206/501, 502, 514, 515; 446/108, 110

[56] References Cited

U.S. PATENT DOCUMENTS

| | | | |
|---|---|---|---|
| 1,569,066 | 1/1926 | Beiger . | |
| 3,653,357 | 4/1972 | Sheidlower et al. | 119/6.5 |
| 3,654,012 | 4/1972 | Schlager | 156/212 |
| 3,695,799 | 10/1972 | Held, Jr. | 425/504 |
| 3,709,426 | 1/1973 | Farkas | 383/49 |
| 4,677,938 | 7/1987 | Tominaga | 119/421 |
| 4,946,414 | 8/1990 | Zimmer | 446/71 |
| 4,953,506 | 9/1990 | Sanders | 119/61 |
| 5,005,524 | 4/1991 | Berry | 119/51.11 |
| 5,409,126 | 4/1995 | DeMars | 220/4.27 |
| 5,575,236 | 11/1996 | Pogue et al. . | |
| 5,619,952 | 4/1997 | Walker | 119/61 |
| 5,779,517 | 7/1998 | Clarke | 446/108 |
| 5,895,624 | 4/1999 | Reece et al. | 264/554 |
| 5,928,599 | 7/1999 | Laphan et al. | 264/516 |

OTHER PUBLICATIONS

EXPLORATOY Product Catalog, 1996.
Educational Insights Buyer's Catalog 1996.
"CRITTER CONDO", Advertisement from Educational Insights Product Catalog.

*Primary Examiner*—Peter M. Poon
*Assistant Examiner*—Yvonne R. Abbott
*Attorney, Agent, or Firm*—Rockey, Milnamow & Katz, Ltd.

[57] ABSTRACT

An ant habitat includes an outer transparent member which is vacuum-formed from a plastic sheet of material to have a through opening with an outer flexible perimeter wall. An inner transparent member having an inner flexible perimeter wall is connected through a flange to the outer transparent member to provide a space between the inner and outer flexible perimeter walls for receiving particulate material that will permit ants to burrow therethrough. The outer transparent member has a retainer lip extending above the inner transparent member to prevent the egress of ants.

21 Claims, 3 Drawing Sheets

ANT HABITAT WITH RETAINER LIP

BACKGROUND OF THE INVENTION

1. Field of the Invention

The present invention is directed to an apparatus for providing an ant habitat to permit the viewing of the insects as they form a colony and tunnel through particulate material and more particularly to an ant habitat housing structure that permits ready access to the habitat while retaining the ants.

2. Description of Related Art

The prior art discloses numerous examples of housing structures used to enable the viewing of insects and ants as they tunnel and build a habitat for their nest. Such structures have been a favorite toy for children for over fifty years, and numerous variations of such structures have been proposed in the art, such as shown in U.S. Pat. No. 5,575,236, which discloses an ant habitat construction of a convex configuration that requires assembly of various component parts of injection molded plastic parts. Frequently, such products include accessory materials, such as water droppers, tunnel starting tools, tweezers, magnifying glasses, etc., as can be seen in the Ant Factory product which is sold by Educational Insights, Inc. of Carson, Calif. Other examples of commercial products are the Critter Carnival and Critter Condo, also sold by Educational Insights, Inc. The Critter Carnival includes a built-in magnifying lens to enable the viewing of the insect inhabitants.

A common design goal for these habitat structures are to maintain the captivity of the insects, such as ants, while maximizing the viewing capability of their activities. Additionally, since this is a competitive market, issues of economics are always important in the construction of such structures.

OBJECTS AND SUMMARY OF THE INVENTION

The present invention comprises a device for providing an insect or ant habitat that includes an outer light-weight transparent member that is connected to a complementary light-weight inner transparent member to provide an intermediate space between the two transparent members that will support particulate material, such as a sand mixture, to permit the insects, such as ants, to burrow therethrough. The outer transparent member is fixed to and encompasses the inner transparent member about its periphery and further extends above and inwardly relative to the inner transparent member to provide an encompassing retainer lip that prohibits the egress of the insect inhabitants, such as ants.

Both the outer transparent member and the inner transparent member have lower supporting flanges that can be permanently connected together to provide both structural integrity and strength in addition to providing a bottom for the intermediate encompassing space. The outer transparent member and the inner transparent member are preferably formed from a pressure or vacuum-forming of thin flat plastic sheets which, when combined, provide a flexible housing with a hollow core for the structure so that the principal accumulation of the particulate material is about the perimeter of the core which provides additional structural strength. The inner transparent member is integrally formed with an upper roof connecting its perimeter side walls with the interior having a somewhat convex configuration with a peripheral flange. The outer transparent member is hollow with a complementary flange to that of the inner transparent member to enable a fastening of the two structures together. The perimeter wall of the outer transparent member extends in a parallel manner adjacent the perimeter wall of the inner transparent member. The perimeter wall of the outer transparent member further vertically extends above the upper roof of the inner transparent member and has an inwardly extending lip or rim that substantially extends over the encompassing perimeter space between the inner and outer transparent members. The configuration of the lip is designed to prevent egress of a popular type of ant from the structure.

A complementary cover member can be removably snapped onto the outer periphery of the perimeter wall of the outer transparent member. The cover member can include a dome-shaped portion that is capable of mounting an optical member, such as a plastic lens, to permit an enlargement or magnification viewing of the surface of the interior to better observe the insect inhabitants. The upper roof member of the inner transparent member can be appropriately indented for receiving particulate material and can support accessory items, such as a water container. Additionally, a source of light can be positioned within the hollow interior to facilitate observation of the tunnels while an auxiliary microscope can be used to permit close observation of the insects.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Figure 1:
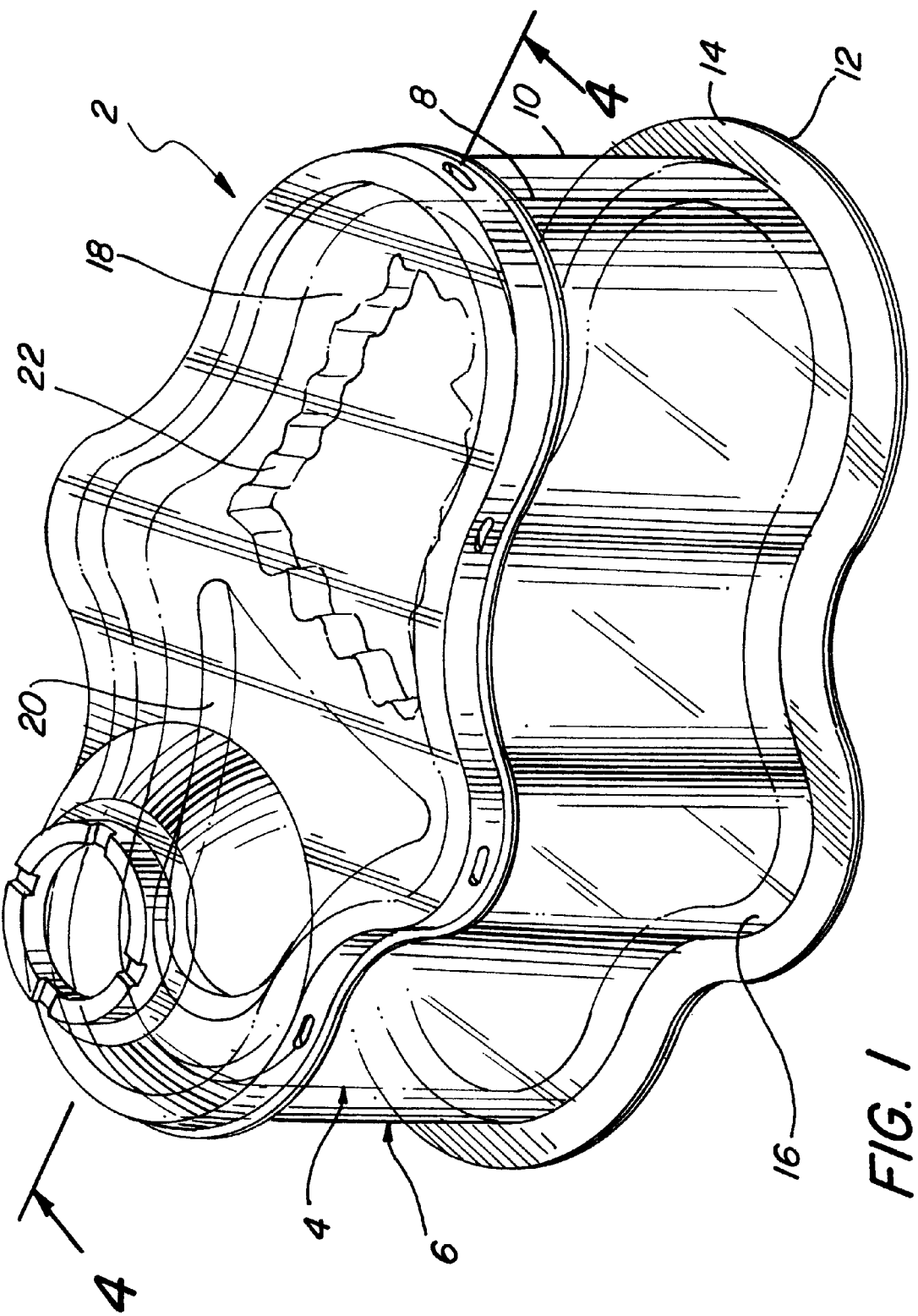
FIG. 1 is a perspective view of the ant habitat of the present invention.

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide an inexpensive ant habitat with a retainer lip.

The present invention is directed to providing a relatively economical light-weight housing structure that is capable of holding a particulate material, such as a sand mixture, to create an ant habitat. The components of the housing member can be economically produced from three vacuum or pressure molded sheets of transparent plastic, such as a polyvinyl chloride sheet of approximately 0.03 inches in thickness. The particular design of the individual components ensures a composite strength greater than the individual components, while the weight of the particulate material adds a feeling of substance to the resulting structure with substantial stability to prevent overturning or flexing, for example, during play action with a child.

Referring to FIGS. 1–4, the transparent plastic housing member 2 includes an inner transparent core member 4 and an outer transparent member 6. While the envelope of these members 4 and 6 can be subjectively configured, and only the preferred embodiment is disclosed herein, it is contemplated that the respective perimeter walls 8 of the inner transparent core member 4 and perimeter walls 10 of the outer transparent member 6 will be approximately parallel to each other with a slight draft or inclination to accommodate a vacuum-forming procedure. The respective perimeter walls in the preferred embodiment have a sinusoidal configuration that provides four exterior curves and four convex indentations that are symmetrical about a longitudinal axis of the structure.

The inner transparent core member 4 has a lower flange 12 that extends at approximately an angle of 90° outward from a base of the perimeter wall 8. Likewise, the outer transparent member 6 has a lower flange member 14 that also extends at approximately a 90° angle from a base of the perimeter wall 10, but as can be seen from FIG. 3, the width of the lower flange 14 is substantially less than the width of the lower flange 12. The differences in the widths of the respective lower flanges 12 and 14 define the Sickness of an intermediate space 16 that extends annularly between the respective perimeter walls 8 and 10. This space 16 is designed to receive particulate material 54, such as a sand mixture, and will provide the primary viewing volume for the tunnels that the ants will usually construct in forming a nest. The first lower flange 14 and the second lower flange 12 can be fastened together by ultrasonic welding or by an adhesive fastener to form the support or base for the housing member 2.

The inner transparent core member 4 further has a vacuum-formed roof member 18 that can also have subjectively indented patterns, such as the bell pattern 20 and the irregular pattern 22. These patterns or depressions can also be covered with the particulate material 54 and can also be used to form the basis of supporting a container or cup member 24 that can hold water for the colony of ants.

Figure 2:
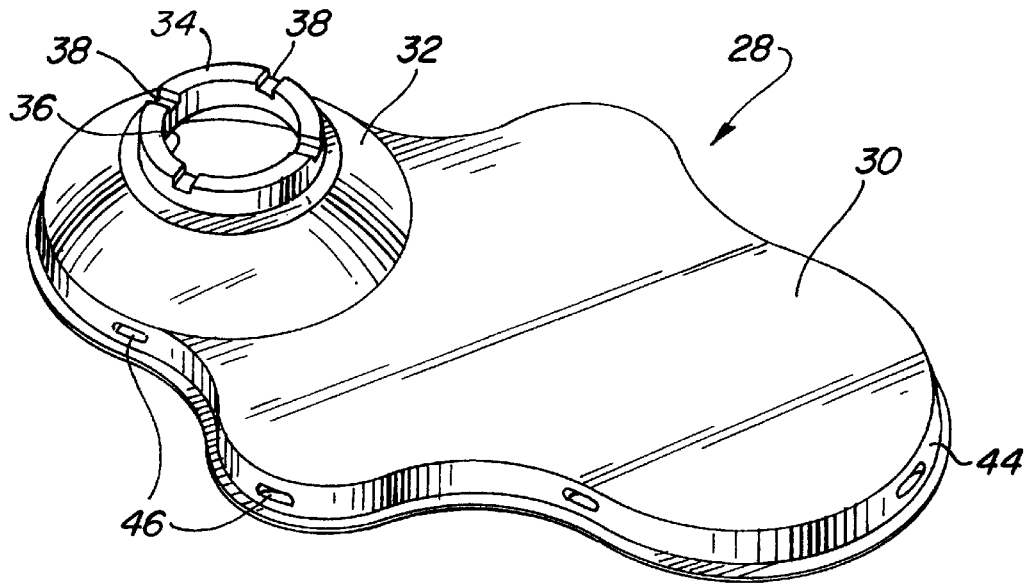
FIG. 2 is a perspective view of the cover member.
Figures 4, 5:
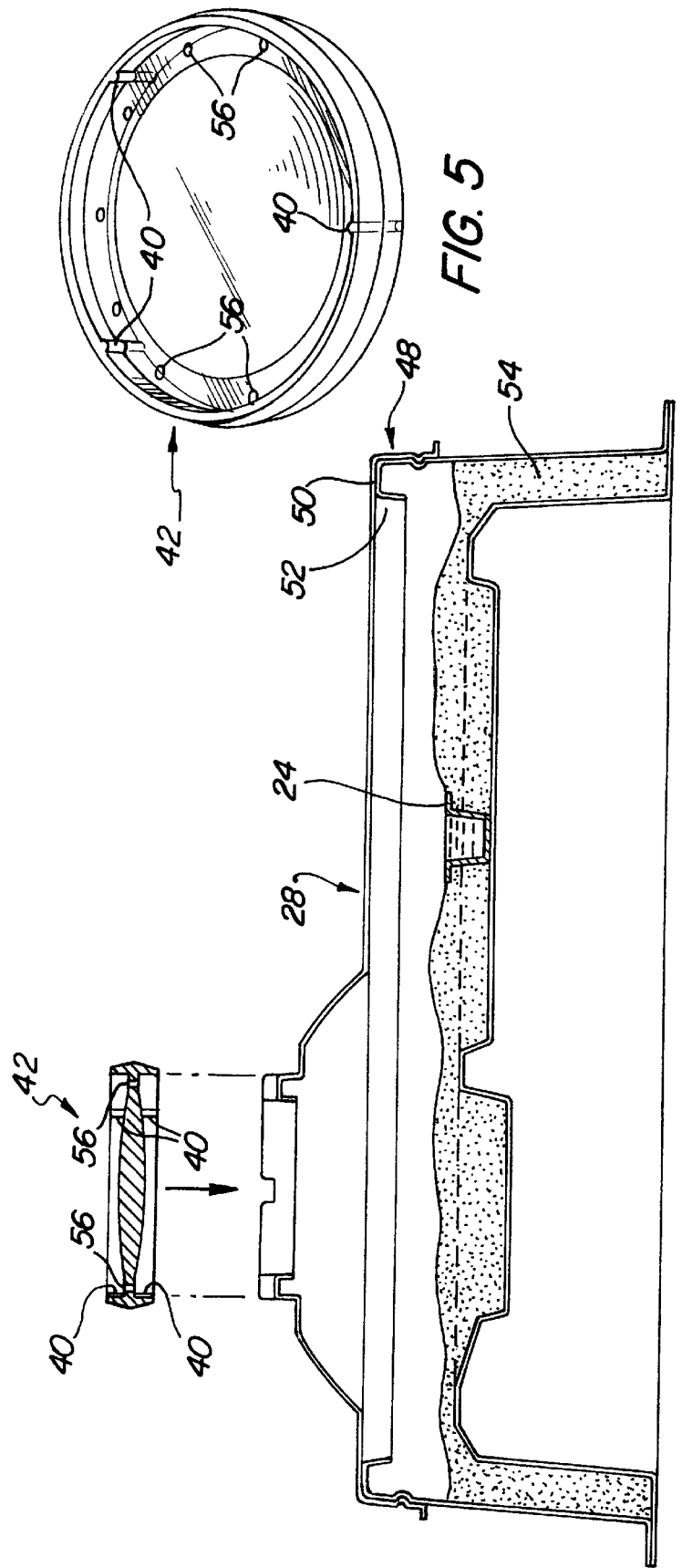
FIG. 4 is a cross-sectional view of the ant habitat taken along the lines 4—4 of FIG. 1.
FIG. 5 is a perspective view of a magnification lens.

The perimeter wall 10 of the outer transparent member 6 has a series of appropriate locking indentations 26 that are spaced about an upper edge of the perimeter wall 10. As seen in FIG. 2, a cover member 28 can also appropriately be formed by a pressure vacuum-forming process to complement the upper perimeter of the outer transparent member 6. The upper surface of the cover member 28 is planar at one end 30 and has a dome configuration 32 at the other end. The dome configuration 32 includes a mounting rim 34 that extends about an aperture opening 36. A series of notches 38 are designed to cooperate with mounting posts 40 that are located on the interior rim of a plastic magnifying lens 42, as seen in FIG. 5 and to provide ventilation. One mounting post 40 will align with a notch 38 to locate the plastic magnifying lens 42 while the remaining posts 40 will bear against the exterior of the mounting rim 34 to bias the lens 42 into a removable position in the mounting rim 34.

The magnifying lens 42 is preferably made from an injection molded plastic with the relative height of the dome configuration 32 and the focal length of the magnifying lens 42 providing an appropriate magnification of the surface structure beneath the magnifying lens 42, as shown, for example, in FIG. 4. Vent holes 56 can be provided about the lens 42 to supplement the ventilation of the notches 38.

The cover member 28 includes a perimeter wall 44 that extends at approximately a 90° angle from the plane of the planar surface 30. Complementary indentations 46 match the locking detents 26 on the outer transparent member 6. Thus, the cover member 28 can be easily snapped onto the outer transparent member 6, while permitting an easy removal of the cover member 28. The respective indentations and detents are designed to nest together in a locking action, as seen in FIG. 4.

Figure 3:
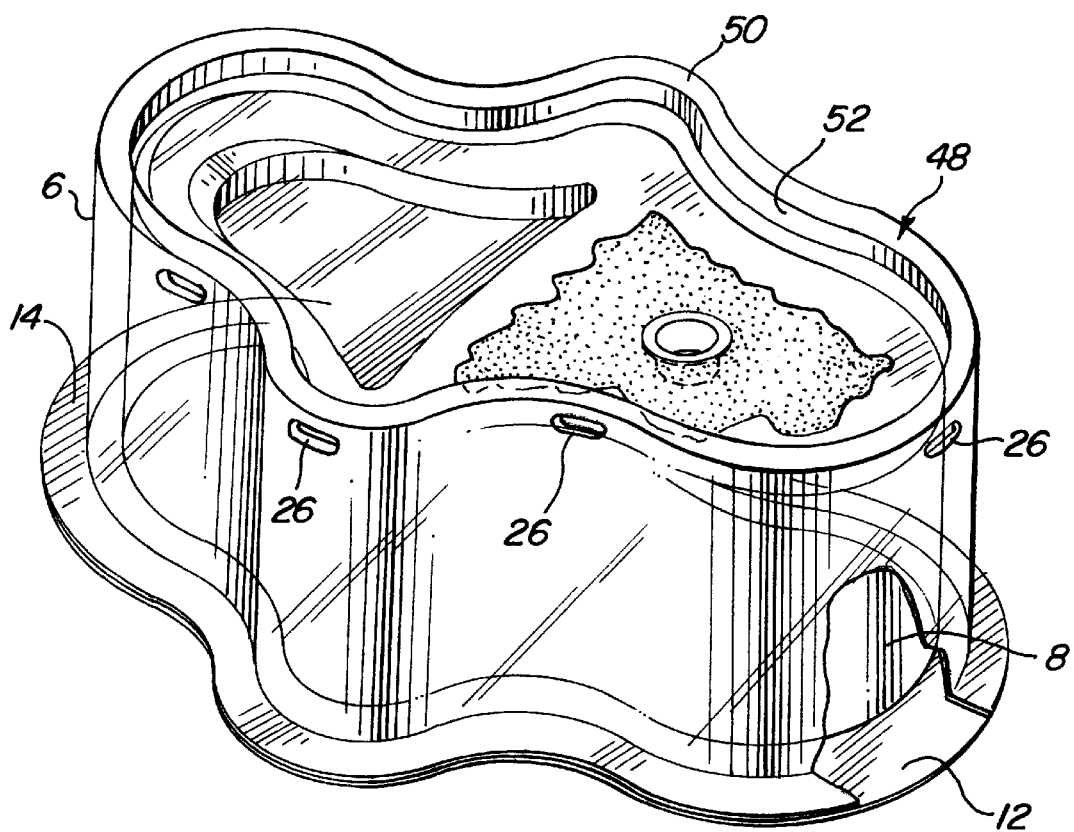
FIG. 3 is a perspective view of the ant habitat constructed from the outer and inner transparent members.

Referring to FIG. 4, a cross-sectional view of the upper retaining rim or lip 48 of the outer transparent member 6 is disclosed. The rim 48 extends inward from the perimeter wall 10 to provide a flat horizontal support surface 50 for the cover member 28. A flange portion 52 extends at approximately a 90° angle downward from the support surface 50, and this structure plus the surface slipperiness of the PVC outer transparent member 6 prevents the insects, and particularly ants, from egressing from their habitat. Thus, while it is desirable to maintain the cover member 28 mounted on the outer transparent member 6, thereby preventing dust and debris from spoiling the ants' habitat, the cover member can be removed, as shown in FIG. 3, and the rim or lip 48 with its downwardly extending flange 52 can be relied upon to ensure that the species of ants will not escape. This design feature has been effective with harvester ants known scientifically as Pogonomyrmex Californica.

As can be further seen in FIG. 4, the particulate material, such as sand 54, can fill the space 16 and can further extend over the upper roof member 18 to provide tunneling material for the ants when they are introduced into this habitat. The particulate material 54 can also, provide a support for an auxiliary water container 24 to hold water for the ants. Since the sand will occupy the space between the respective perimeter walls 8 and 10, the center of gravity of the housing member 2 will be relatively low and provides a stable platform for the structure. The inner transparent core member 4 has roughly a lower convex configuration and a source of light can be inserted within the resulting hollow space to provide some illumination for viewing the tunneling of the ants. Since the component parts with the exception of the injection molded plastic magnifying lens 42 is formed from relatively inexpensive thin sheets of PVC material by a vacuum-forming process, a relatively economical structure can be assembled from only three component parts, namely the inner transparent core member 4, which is permanently adhered to the outer transparent member 6 with a removable cover member 28 that can be easily snapped on and off the ant habitat. By simply introducing the particulate material 54 plus a supply of ants, a workable ant habitat is established for a very economical expenditure.

The provision of the rim or lip configuration 48 with its downwardly extending flange 52 will prohibit the escape of the ants, as long as the ants do not move the particulate material 54 to contact an inner perimeter of the flange 52, that is, as long as the ants do not build up the sand to permit an escape by removing the consequences of the slippery inverted lip, that prohibits their escape.

The particular configuration of the outer perimeter walls can be varied to other subjective configuration. The sinusoidal configuration of the preferred walls not only encourages a strengthening of the structure, but provides a pleasing viewing surface for the observer.

Finally, the ant habitat can be sold in a kit form with the conventional accessory items, such as tweezers for moving the ants, miniature microscopes, and other conventional accessories that are frequently found in the prior art.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A device for providing an ant habitat comprising:

an outer transparent member; and an inner member, the outer transparent member is connected to the inner member and provides a space encompassing the inner member to receive a medium to permit the ants to burrow through, the outer transparent member extends above the inner member and has an inwardly extending encompassing lip that prohibits the egress of the ants, wherein the outer transparent member has a first lower flange and the inner member has a second lower flange, and the respective flanges are connected together to provide a bottom to the encompassing space.

2. The invention of claim 1 further including a roof member for enclosing the top of the inner member.

3. The invention of claim 2 wherein the outer transparent member and the inner members are vacuum-formed from thin plastic sheets.

4. The invention of claim 1 further including a cover member that is configured to removably attach to the outer transparent member.

5. The invention of claim 4 wherein the outer transparent member has a series of indents and the cover member has a complementary series of indents to removably lock the cover member to the outer transparent member.

6. The invention of claim 4 wherein the cover member includes a dome-shaped portion.

7. The invention of claim 6 wherein a magnification lens is mounted on the dome-shaped portion.

8. The invention of claim 1 wherein the outer transparent member has an outer perimeter wall and the inner member has an inner perimeter wall which is approximately parallel to the outer perimeter wall.

9. A device for providing an ant habitat comprising:

an outer transparent member; and an inner transparent member, the outer transparent member is connected to the inner transparent member and provides a space encompassing the inner transparent member to receive a medium to permit the ants to burrow through, the outer transparent member extends above the inner transparent member and has an inwardly extending encompassing lip that prohibits the egress of the ants, wherein the outer transparent member has a first lower flange and the inner transparent member has a second lower flange, and the respective flanges are connected together to provide a bottom to the encompassing space.

10. A device for providing an ant habitat comprising:

an outer transparent member having a through opening with an outer flexible plastic perimeter wall;

an inner transparent member having an inner flexible plastic perimeter wall, the outer transparent member is connected to the inner transparent member to provide a space between the inner and outer flexible perimeter walls, the space is configured to encompass the inner transparent member; and a particulate material positioned within the space and supporting the respective perimeter walls to limit the flexion permitted.

11. The invention of claim 10 wherein the outer transparent member extends above the inner transparent member and has an inwardly extending encompassing lip that prohibits the egress of the ants.

12. The invention of claim 11, wherein the outer transparent member has a first lower flange and the inner transparent member has a second lower flange, and the respective flanges are connected together to provide a bottom to the encompassing space.

13. The invention of claim 12 further including a roof member for enclosing the top of the inner transparent member.

14. The invention of claim 13 wherein the outer transparent member and the inner transparent members are vacuum-formed from thin transparent plastic sheets of approximately 0.03 inches of thickness.

15. The invention of claim 14 further including a cover member that is configured to removably attach to the outer transparent member.

16. The invention of claim 15 wherein the outer transparent member has a series of indents and the cover member has a complementary series of indents to removably lock the cover member to the outer transparent member.

17. The invention of claim 15 wherein the cover member includes a dome-shaped portion.

18. The invention of claim 17 wherein a magnification lens is mounted on the dome-shaped portion.

19. The invention of claim 14 wherein the outer transparent member has an outer perimeter wall and the inner transparent member has an inner perimeter wall which is approximately parallel to the outer perimeter wall.

20. A device for providing an insect habitat comprising:

an outer transparent member having a through opening with an outer flexible plastic perimeter wall;

an inner member having an inner flexible plastic perimeter wall, the outer transparent member is connected to the inner member to provide a space between the inner and outer flexible perimeter walls, the space is configured to encompass the inner member; and a particulate material positioned within the space and supporting the respective perimeter walls to limit the flexion permitted, wherein the outer transparent member has a first lower flange and the inner member has a second lower flange, and the respective flanges are connected together to provide a bottom to the encompassing space.

21. The invention of claim 20, wherein the outer member and the inner member are thin flexible plastic sheets, whereby the medium will support and limit the flexion of the plastic sheets when the medium is inserted in the space between them.

* * * * *